United States Patent [19]

McVicker

[11] 3,968,128

[45] July 6, 1976

[54] MAGNESIUM-GROUP VIII TRANSITION METAL CARBONYL AND SUBSTITUTED CARBONYL COMPLEXES

[75] Inventor: Gary B. McVicker, Westfield, N.J.

[73] Assignee: Exxon Research and Engineering Company, Linden, N.J.

[22] Filed: Nov. 27, 1973

[21] Appl. No.: 419,367

Related U.S. Application Data

[63] Continuation-in-part of Ser. No. 51,669, July 1, 1970, abandoned.

[52] U.S. Cl. ..................... 260/347.8; 260/346.1 M; 260/270 R; 260/429 CY; 260/429 R; 260/439 CY; 260/439 R; 260/604 HF; 260/632 HF; 260/666 B; 252/431 R; 252/431 N; 252/431 P
[51] Int. Cl.$^2$ ..................... C07D 307/04
[58] Field of Search ................. 260/346.1 M, 347.8, 260/439 CY, 439 R, 429 R, 429 CY

[56] References Cited
OTHER PUBLICATIONS

Hieber et al., (I) Zeitschrift fur Anorganische and Allegemeine Chemie, Mar. 1962, vol. 314, pp. 125–143.

Burlitch et al., Journal of Organometallic Chem. (1969) vol. 19, pp. 21–23.

Hieber et al., (ii), Chem. Ber. (1961) vol. 94, pp. 1417–1425.

Primary Examiner—Henry R. Jiles
Assistant Examiner—Bernard Dentz
Attorney, Agent, or Firm—Robert J. Baran

[57] ABSTRACT

The preparation of novel compounds of the general formula $B_xMe(M)_2$ is described; wherein B is a Lewis base, x is an integer 1 through 4, Me is a Group IIA metal, and M is a transition metal carbonyl or a substituted transition metal carbonyl group. These compounds are shown to have utility as catalysts for hydrogenation, butadiene oligomerization, carbonylation, isomerization and hydroformylation. In a preferred embodiment the tetrakis tetrahydrofuran adduct of the magnesium-cobalt phosphine substituted carbonyl complex is shown to effectively catalyze the hydroformylation of 1-hexene.

7 Claims, No Drawings

– 1 –

MAGNESIUM-GROUP VIII TRANSITION METAL CARBONYL AND SUBSTITUTED CARBONYL COMPLEXES

CROSS REFERENCE TO RELATED APPLICATIONS

This application is a continuation-in-part application of Ser. No. 51,669, filed July 1, 1970 now abandoned.

FIELD OF THE INVENTION

This invention relates to novel compounds which are shown to have utility as catalysts for hydrogenation, butadiene oligomerization, and hydroformylation. More particularly, this invention relates to the preparation of novel compounds of the general formula $B_xMe(M)_2$, wherein B is a Lewis base, x is an integer from 1 to 4, Me is a metal chosen from Group IIA of the Periodic Table of the Elements, and M is a transition metal carbonyl or a substituted transition metal carbonyl group, and in particular wherein Me is magnesium.

In a preferred embodiment, 1-hexene is contacted with hydrogen and carbon monoxide in the presence of the tetrakis tetrahydrofuran adduct of magnesium-cobalt substituted carbonyl complex at a pressure of 1,500 lbs. and a temperature of 140°C., to give >99% conversion to heptaldehydes and heptylalcohols, with a selectivity of 87% aldehyde.

PRIOR ART

The covalent nature of bonds between main group elements and transition metals has been well established by numerous chemical, structural, and spectroscopic investigations. Many compounds are known in which a main Group IVA or IIB metal is covalently bonded to a transition metal. Cases in which a transition metal is bonded to an element of main Group IIA or IIIA are, by contrast, few in number. Group IA transition metal compounds are known but are essentially ionic and are generally not isolatable and are handled only as solutions in polar solvents.

It is generally found that the covalent nature of a main Group IIIA or main Group IVA metal bonded to a transition metal decreases as one moves from Group IVA to Group IIIA or ascends either respective group. This trend in covalent bonding is responsible for the failure of the early numbers of Group IIIA to form easily isolable compounds with transition metals (the transition metal anion is the seat of reactivity and is readily attacked by electrophiles).

Group IIA-transition metal compounds have been described in two instances, but in both cases hereafter noted the proposed composition and structure was incorrectly postulated. Von W. Hieber et al, in the March 1962 issue of Zeitschrift fur anorganische and allgemeine Chemie, pp. 125-143, describes the reaction of a dimeric manganese carbonyl complex with magnesium amalgam in the presence of tetrahydrofuran to give the bis-tetrahydrofuran adduct of magnesium-manganese carbonyl complex. As will be elucidated herein, this product is not produced under the reaction conditions described; instead the tetrakis adduct is obtained in quantitative yield. Furthermore, Hieber et al teach a method for preparing the complex $(C_4H_8O)_2Mg[Mn(CO_4)P(C_6H_5)_3]_2$; only. The stability of this complex is largely due to the stabilizing effect of the phosphine ligand $P(C_6H_5)_3$. The ability of $P(C_6H_5)_3$ to impart thermal stability to carbonyl complexes is well documented in the literature. The instant disclosure describes the preparation of non-phosphine complexed compounds, e.g., $(C_4H_8O)_4Mg[Mn(CO)_5]_2$. The isolation of this complex was totally not expected because of the absence of the stabilizing phosphine ligand. Burlitch and Ulmer, in the Journal of Organometallic Chemistry, 19 (1969), pp. 21-23, describe the preparation of halides of magnesium transition metal carbonyl complexes (transition metal carbonyl Grignard reagents) by the reaction of the transition metal carbonyl halide with magnesium in the presence of tetrahydrofuran. The authors did not isolate these products, but inferred that they existed by the further reactions of the unisolated complex. As will again be elucidated hereafter, it can be shown that halide derivatives of magnesium-transition metal carbonyl complexes cannot be isolated, but, instead, if formed, immediately disproportionate to give bis-transition metal derivatives of magnesium complexed with Lewis base molecules and magnesium halide.

Group IIA-transition metal compounds would be expected to be more ionic in nature than the corresponding IIB derivatives. A balance between covalent and ionic bonding contributions to the hetero metal-metal bond is needed to insure reasonable solubility in organic solvents. Hydrocarbon solubility is, of course, a necessity for use of the Group IIA-transition metal compound as a homogenous catalyst for hydrogenation, polymerization, dimerization, and hydroformylation reactions.

SUMMARY OF THE INVENTION

According to this invention, it has been unexpectedly found that a transition metal carbonyl can be reacted with a metal chosen from Group IIA of the Periodic Table of the Elements in the presence of a Lewis base, to give novel compounds, wherein the transition metal is bonded directly to the Group IIA metal. This reaction is effected, preferably, by the reaction of an amalgam of the Group IIA metal with a dimeric transition metal carbonyl complex, but other preparations for the novel compounds are discussed hereinafter.

The novel compounds will have the general formula:

$$B_xMe(M)_2$$

wherein B is a Lewis base; x is an integer (from 1 to 4); Me is a Group IIA metal; and M is a transition metal carbonyl or substituted transition metal carbonyl complex.

Any Lewis base capable of coordinating with a Group IIA metal is within the scope of the instant invention, but organic nitrogen bases, including ammonia, and oxygenated hydrocarbons, e.g. ethers and ketones, are preferred, with compounds such as pyridine, tetrahydrofuran, and tetramethyl ethylene diamine most preferred. x relates to the number of Lewis base molecules needed to complete the coordination sphere of the Group IIA metal, and will usually equal 2 or 4, but could be 1 if a tetradentate Lewis base were employed in the place of 4 monofunctional bases.

The number of complexed Lewis bases, i.e. the number of oxygen or nitrogen atoms required to stabilize the group IIA metal-transition metal compounds varies with the nucleophilicity of the transition metal complexes. When the transition metal residue is a strongly nucleophilic anion, such as $-Fe(CO)_2C_5H_5$, complexes containing two monofunctional Lewis bases (two oxygen or nitrogen heteroatoms may also be supplied by one bifunctional Lewis base) are prepared, while less nucleophilic anions, such as $-Co(CO)_4$ yield Group IIA derivatives containing four monofunctional complexed Lewis bases or two bifunctional or one tetrafunctional complexed Lewis bases.

The total number of coordinated groups around Me (the Group IIA metal) can be either 4 (tetrahedral) or 6 (octahedral). In the case of 4 groups coordinated about Me, the subscript ($x$) is two and cn be filled with either two monofunctional oxygenated hydrocarbons or organic nitrogen bases, or one bifunctional oxygenated hydrocarbon or organic nitrogen base (wherein both oxygen or nitrogen atoms of the bifunctional Lewis base are coordinated to the Me atom), e.g.,

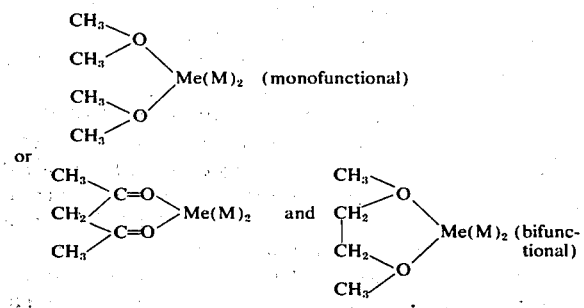

In the case of 6 groups coordinated about Me, ($x$) is 4 and can be filled with, for example, 4 monofunctional oxygenated hydrocarbons, 2 bifunctional oxygenated hydrocarbons or one tetrafunctional oxygenated hydrocarbon. Alternatively, organic nitrogen bases may be used as coordinated groups.

An example of a suitable tetrafunctional oxygenated hydrocarbon would be $CH_3OCH_2CH_2OCH_2CH_2OCH_2CH_2OCH_3$ (triglyme).

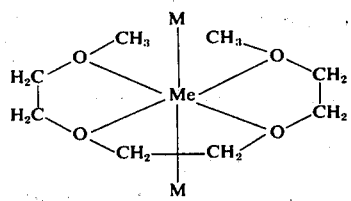

In general, the preferred class of oxygenated hydrocarbons which are useful Lewis bases for forming the complexes of this invention are selected from the group consisting of compounds represented by the general formulae:

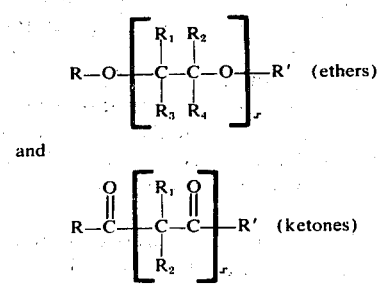

wherein R and R' are $C_1$ to $C_{10}$ hydrocarbon radicals, and may be selected from the group consisting of normal, branched, and cyclic alkyl groups, and aromatic, including alkaryl and aralkyl groups; $R_1$, $R_2$, $R_3$ and $R_4$ are selected from the group consisting of hydrogen and $C_1$ to $C_4$ alkyl groups; and $x$ is an integer of from 0–3. Preferably, R and R' are selected from the group consisting of $C_1$ to $C_{10}$ alkyl groups, $C_5$ to $C_{10}$ cycloalkyl groups, $C_6$ to $C_{10}$ aromatic groups, and $C_7$ to $C_{10}$ alkaryl and aralkyl groups, and $R_1$, $R_2$, $R_3$ and $R_4$ are hydrogen. When $x$ is O, R and R' together may form a ring which may or may not include the oxygen, e.g., as in tetrahydrofuran and cyclohexanone.

Examples of mono-, bi- and tetrafunctional oxygenated hydrocarbons which can coordinate to Me through a lone pair of electrons thereby stabilizing the Group IIA metal-transition metal complexes are listed below.

Mono functional oxygenated hydrocarbons

Ethers:

Tetrahydrofuran
Tetrahydropyran
Dioxane
Diethyl ether
Dipropyl ether
Methyl ethyl ether
Dicyclohexyl ether
Diphenyl ether
Methyl phenyl ether ketones:

Acetone
Methyl ethyl ketone
Dicyclohexyl ketone
Methyl cyclohexyl ketone
Diphenyl ketone
Cyclohexanone
Methyl phenyl ketone Difunctional oxygenated hydrocarbons:

Diethers:

$CH_3OCH_2CH_2OCH_3$ (glyme)
$CH_3CH_2OCH_2CH_2OCH_2CH_3$ (1,2-di-ethoxyethane)
$C_3H_7OCH_2CH_2OCH_2CH_3$ (1-propoxy-2-ethoxyethane)
$C_6H_5OCH_2CH_2OC_6H_5$ (1,2-diphenoxy-ethane)

Diketones:

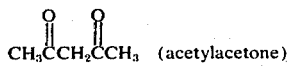

 1,2-cyclohexandione
1,3-cyclohexandione

Tetrafunctional oxygenated hydrocarbons

Tetraethers:

$CH_3OCH_2CH_2OCH_2CH_2OCH_2CH_2OCH_3$ (triglyme)

Tetraketone:

2,4,6,8-n-nonatetraone

The preferred class of organic nitrogen bases which are within the scope of this inventon, i.e. they stabilize the Group IIA transition metal compounds are selected from compounds represented by the general formulae:

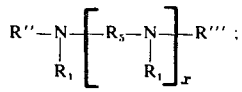

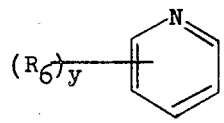

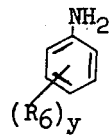 ; and 2,2'-bipyridyl; and
1,10 phenanthroline
wherein R'' and R''' are selected from the group consisting of hydrogen and $C_1$ to $C_{10}$ hydrocarbyl radicals, preferably $C_1$ to $C_5$ alkyl radicals; $R_1$ is as defined above; $R_5$ is selected from the group consisting of radicals represented by the general formulae:

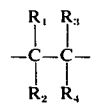 and 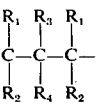

wherein $R_1$, $R_2$, $R_3$ and $R_4$ are as defined above; $R_6$ is a $C_1$ to $C_{10}$ hydrocarbyl radical, preferably a $C_1$ to $C_{10}$ alkyl radical; and y is an integer of from 0 to 5, preferably 0 or 1. Preferred examples of organic nitrogen bases which are within the above description include:

Monofunctional nitrogeneous bases
Ammonia
Methyl amine
Dimethyl amine
Trimethyl amine
Triethylamine
Methyl diethylamine
Pyridine
N-decyl pyridine
Aniline Bifunctional nitrogeneous bases 2,2-bipyridyl
1,10-phenanthroline
Ethylene diamine
tetramethylenediamine
1,3-propylene diamine Tetrafunctional nitrogeneous bases

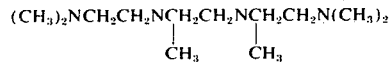

Hexamethyltriethylenetetramine
Triethylenetetramine

Me represents the Group IIA metal, which is preferably magnesium.

M represents the transition metal carbonyl or substituted transition metal carbonyl complex which will have the general formula $(Me'CO_aL_b)$ wherein: Me' is a transition metal selected from Groups V, VII and VIII of the Periodic Table of the Elements, with metals selected from Groups VIB and VIII preferred, and Fe, Mo, Co, Rh and Ni most preferred; $a$ is an integer ranging from 1 to 5, $b$ is an integer ranging from 0–4, and $a$ and $b$ total 5 or less; and L can be a uni- or polydentate Lewis base ligand capable of coordinating with the transition metal or a hydrocarbon residue such as cyclopentadienyl.

When Me' is a Group VIII metal, $a$ and $b$ equal 4 or less; while when Me' is a Group VI or Group VII metal, $a$ and $b$ equal 5 or less.

L is preferably selected from compounds of the group having the following general formulae:

(I) 

and $$R'_1-X-R'_2 \quad \text{(II)}$$
$$\phantom{R'_1-}R'_3$$

wherein $R'_4$, $R'_1$, $R'_2$ and $R'_3$ are hydrocarbyl radicals independently selected from the group consisting of hydrogen, alkyl, cycloalkyl, aralkyl, aryl and alkaryl with hydrogen, preferably $C_1$ to $C_{10}$ alkyl, $C_3$ to $C_{10}$ cycloalkyl, $C_6$ to $C_{10}$ aryl, and $C_7$ to $C_{10}$ aralkyl and alkaryl and hydrogen, $C_1$ to $C_{10}$ alkyl, and $C_6$ to $C_{10}$ aryl most preferred, and X is selected from the group consisting of P and As with P preferred. When Me' is a Group VII metal, X is As; preferably, when Me' is a Group VII metal, $b$ is 0.

Thus, compounds within the scope of this definition include: cyclopentadiene, methyl cyclopentadien, ethyl cyclopentadiene, butyl cyclopentadiene, phosphine, trimethyl phosphine, triethyl phosphine, tributyl phosphine, methyl diphenyl phosphine, triphenyl phosphine, butyl diphenyl phosphine, triethylamine, triethylarsine and triethylstibine, etc.

L may also represent more than one ligand independently selected from the above group. For example, in the compound $[C_4H_8O]_4Mg[Mo(CO)_2(PCH_3(C_6H_5)_2)C_5H_5]_2$, wherein a would equal 2, and L would equal methyl diphenyl phosphine and cyclopentadiene.

The above-mentioned novel compounds can be prepared by any of four methods:

1. A slight excess of $MeX_2$ (wherein Me is a Group IIA metal and X is Cl, Br or I, preferably Cl or Br) dissolved in tetrahydrofurn (THF) can be added to the Na derivative of the transition metal carbonyl complex, with agitation. After the reaction is complete, the crude reaction mixture is filtered to remove the insoluble NaX formed. The filtrate is concentrated with reduced pressure and the magnesium transition metal compound is precipitated by adding n-pentane. The solid product is purified by recrystallization from benzene.

Examples of some sodium derivatives of transition metal carbonyl complexes include:

Na⊕Fe(CO)₂(C₅H₅)⊖

Na⊕Mo(CO)₃(C₅H₅)⊖

Na⊕Co(CO)₄⊖

Na⊕(Co(CO)₃(P(nC₄H₉)₃))⊖

Examples of reaction pathways:

MgCl₂ + Na[Co(CO)₃P(nC₄H₉)₃] $\xrightarrow{THF}$ (THF)₄Mg[Co(CO)₃P(C₄H₉)₃]₂ + 2NaCl BeCl₂ + NaCo(CO)₄ $\xrightarrow{THF}$ (THF)₂Be(Co(CO)₄)₂ + 2NaCl 2. A solution of a transition metal carbonyl derivative of Hg is reacted with the Group IIA metal. The crude reaction mixture is filtered to remove the free mercury formed by the metal exchange reaction. The magnesium transition metal compound is isolated from the filtrate as in (1) above. Examples of some Hg derivatives of transition metal carbonyl complexes include:

Hg(Fe(CO)₂C₅H₅)₂

Hg(Co(CO)₄)₂

Hg(Co(CO)₃P(C₆H₅)₃)₂

Hg(Mo(CO)₃C₅H₅)₂

Typical reaction pathway:

Hg(Fe(CO)₂C₅H₅)₂ + Mg° $\xrightarrow{THF}$ (THF)₂Mg(Fe(CO)₂C₅H₅)₂ + Hg°

3. The same procedure as in (2), except that a transition metal carbonyl halide compound is used instead of the mercury derivative. The Group IIA halide formed is removed by filtration. Examples of some transition metal carbonyl halides include:

(C₅H₅)Fe(CO)₂I, (C₅H₅)Fe(CO)₂Br (C₅H₅)Mo(CO)₃I (C₅H₅)Mo(P(nC₄H₉)₃)(CO)₂I (C₅H₅)Ni(CO)I ((C₆H₅)₃P)₂Rh(CO)Cl (CO)₅MnBr

Typical reaction pathway:

2(C₅H₅)Fe(CO)₂I + 2Mg $\xrightarrow{THF}$ (THF)₂Mg(Fe(CO)₂C₅H₅)₂ + MgI₂

4. An amalgam of the Group IIA metal is reacted with a dimeric metal carbonyl complex yielding the above mentioned novel compounds. Examples of some dimeric metal carbonyl complexes include:

(Fe(CO)₂(C₅H₅))₂

(Mo(CO)₃(C₅H₅))₂

((C₅H₅)Ni(CO))₂

Co₂(CO)₈

Co₂(CO)₆(P(nC₄H₉)₃)₂

Mn₂(CO)₁₀

(W(CO)₃C₅H₅)₂

Typical reaction pathway:

Co₂(CO)₆(P(nC₄H₉)₃)₂ + Mg(Hg) $\xrightarrow{THF}$ (THF)₄Mg[Co(CO)₃P(nC₄H₉)₃]₂

All of the above procedures are carried out under an inert atmosphere, generally nitrogen. The reaction temperature range varies from −40°C. to 200°C., preferably between 0°C. and 120°C., and most preferably between room temperature and 100°C.

The reaction of the Group IIA metal (and also the halide or amalgam as shown above) and the transition metal carbonyl complex normally takes place in a solvent. Inert solvents such as benzene, toluene, n-pentane, etc., can be used as long as there is also present enough Lewis base such as pyridine, tetrahydrofuran, etc., to coordinate with the Group IIA metal, as noted above. Preferably, the reaction is carried out in the presence of a substantial excess of the Lewis base, and if the reactants are soluble in the Lewis base, the solvent can consist entirely of the Lewis base. It should be noted that the solubility of the Group IIA-transition metal carbonyl complex in hydrocarbon solvents is dependent on the nature of the Lewis base adduct. For example, in benzene the solubility of the Lewis acid adducts increase in the following order: tetrahydrofuran, pyridine, and tetramethyl ethylene diamine.

The molar ratio of Group IIA metal and transition metal carbonyl complex is preferably greater than 1, since traces of oxygen will cause oxidation of the Group IIA-transition metal carbonyl complex according to the following reaction:

B$_x$Me(M)₂ + ½ O₂ → xB + MeO + M—M wherein the symbols have the meanings ascribed previously.

If the Group IIA metal is in excess, it will convert the transition metal carbonyl dimer back to the desired product according to the following reaction:

M—M + Me $\xrightarrow{(B)}$ B$_x$Me[M]₂

The MeO is easily separable since it will usually be a filterable solid. Also, if the transition metal carbonyl complex is in excess, the unreacted portion will be difficult to remove from the desired Group IIA-transition metal carbonyl compound.

For the above reasons, the mole ratio of Group IIA metal to transition metal usually ranges from 1 to 100 with a range of 1.1 to 10 preferred, and 1.1 to 3 especially preferred. It should be noted that if one does not intend to isolate the product, or does not find the economics, of separating the desired products from the reactants, unattractive, lower ratios may be used.

The catalyst of this invention may be used in a variety of chemical processes. For example, unsaturated organic compounds can be hydrogenated to give the corresponding saturated derivatives. This catalyst is also useful for hydroformylation reactions wherein an alkene is reacted with carbon monoxide and hydrogen to form aldehydes and alcohols. Excellent selectivity has been shown by the tetrakis tetrahydrofuran adduct of magnesium-dicobalt hexacarbonyl bis-methyl diphenyl phosphine in the conversion of 1-hexene to heptaldehydes. The conversion was > 99% with a selectivity of 87%. This conversion is run at elevated pressures, preferably from 1,500 to 3,000 psi. Reaction temperatures will range from 50°C. to 20°C., with a range of 100°C. to 150°C. preferred. Ratio of $H_2$ to CO used will vary with reaction conditions; preferably a 1 to 1 ratio is maintained. The catalyst concentration will range from 0.01 to 20% based on the weight feed, with 0.05 to 10% preferred.

The catalyst of the instant invention has also shown utility in the preparation of cyclic dimers and trimers of butadiene. In particular, cyclododecatriene may be produced by the trimerization of butadiene.

The carbonylation of methanol to methylacetate and various isomerization reactions are easily effected with the catalysts of this invention.

Reactions which utilize the catalyst of the instant invention will usually be run in the liquid phase; i.e., one advantageous characteristic of the catalyst of this invention is that its solubility in organic solvents can be varied by the proper choice of Lewis base adduct, thereby allowing the skilled artist to design a homogeneous or heterogenous catalyst system. The reactions which utilize the catalyst of this invention will be run at temperatures ranging from −50°C. to 500°C. and pressures ranging from subatmospheric to superatmospheric, according to the specific reaction. The proper temperatures and pressure conditions will be apparent to one skilled in the art. In a like manner, the reaction times and the catalyst concentrations will vary according to the specific reaction, and will also be apparent to the skilled artist.

of $[C_5H_5Fe(CO)_2]_2$ with 1% sodium amalgam. This mixture was allowed to stir at room temperature for 24 hours. The crude reaction mixture was filtered with reduced pressure to remove the insoluble salts formed during the reaction. The filtrate was concentrated with reduced pressure. The concentrate was slowly poured into n-pentane which effected the precipitation of a yellow-orange solid. The crude product was recrystallized several times from benzene and vacuum dried. The pure solid is a bright yellow solid and is extremely air sensitive. Upon atmospheric exposure the magnesium-transition metal compound is quantitatively oxidized to $[C_5H_5Fe(CO)_2]_2$ and MgO. The stoichiometry of the complex was established by nmr and elemental analyses. The composition of all of the following novel products were determined by both nmr and elemental analysis.

All reactions were carried under a nitrogen atmosphere.

Calculated for $[C_4H_8O]_2Mg[Fe(CO_2C_5H_5]_2$: 50.5% C, 4.97% H, 4.59% Mg, 21.6% Fe and a molecular weight of 522.

Found for reaction product: 46.7% C, 4.83% H, 4.64% Mg, 22.5% Fe and a molecular weight of 528 in benzene.

Elemental analyses, molecular weight and color data for the novel compounds synthesized in this and the following examples are given in Table I.

It should be noted that the halide intermediate postulated by Burlich and Ulmer could not be isolated. Spectroscopic studies indicated that such intermediates are transient only, and do not exist in solution in measurable quantities.

TABLE I

ANALYTICAL DATA, MOLECULAR WEIGHTS[a] AND COLORS

| Compound | Color | Calculated % | | | | | | Found % | | | | | | Molecular Weight | |
|---|---|---|---|---|---|---|---|---|---|---|---|---|---|---|---|
| | | C | H | Mg | Me' | P | N | C | H | Mg | Me' | P | N | Calc. | Found |
| $(THF)_2Mg(Fe(CO)_2C_5H_5)_2$ | Yellow | 50.5 | 4.97 | 4.59 | 21.6 | — | — | 46.7 | 4.83 | 4.64 | 22.5 | — | — | 522 | 528 |
| $(Pyridine)_2Mg[Fe(CO)_2C_5H_5]_2$ | Yellow | 53.6 | 3.74 | 4.54 | 20.8 | — | 5.24 | 54.9 | 5.16 | 4.82 | 17.7 | — | 5.76 | 536 | 498 |
| $(THF)_4Mg[Mo(CO)_2PCH_3\text{-}$ $(C_6H_5)_2C_5H_5]_2$ | Light Yellow | 58.6 | 5.83 | 2.10 | 16.8 | 5.41 | — | 58.3 | 5.61 | 3.09 | 17.4 | 62.5 | — | — | — |
| $(THF)_4Mg[Mo(CO)_2P$ $(C_4H_9)_3C_5H_5]_2$ | Yellow | 56.4 | 8.35 | 2.11 | 16.7 | 5.39 | — | 55.9 | 8.37 | 2.37 | 18.1 | 5.51 | — | 1150 | 99 |
| $(Pyridine)_4Mg[Co(CO)_4]_2$ | Yellow | 49.3 | 2.96 | 3.42 | 17.3 | — | 8.22 | 49.4 | 3.26 | 2.91 | 17.1 | — | 7.79 | 682 | 665 |
| $(THF)_4Mg[Co(CO)_3PCH_3$ $(C_6H_5)_2]_2$ | Yellow | 57.6 | 5.83 | 2.40 | 11.8 | 6.20 | — | 55.9 | 6.01 | 2.36 | 11.1 | 6.26 | — | — | — |
| $(THF)_4Mg[Co(CO)_3P(C_4H_9)_3]_2$ | Yellow Green | 55.2 | 8.60 | 2.43 | 11.8 | 6.20 | — | 54.6 | 8.74 | 2.45 | 11.4 | 5.99 | — | 1002 | 310 |
| $(Pyridine)_4Mg[Co(CO)_3PCH_3$ $(C_6H_5)_2]_2$ | Yellow | 60.6 | 4.48 | 2.38 | 11.6 | 5.99 | 5.46 | 58.6 | 4.51 | 2.51 | 11.7 | 5.69 | 5.41 | — | — |
| $(TMEDA)_2Mg[Co(CO)_3PCH_3$ $(C_6H_5)_2]_2$ | Yellow | 56.1 | 6.15 | 2.58 | 12.5 | — | — | 53.5 | 6.14 | 2.66 | 12.9 | — | — | — | — |
| $(THF)_4Mg(Mn(CO)_5)_2$ | Yellow | 44.5 | 4.56 | 3.46 | 15.7 | — | — | 43.7 | 5.26 | 3.91 | 13.6 | — | — | — | — |
| $(THF)_4Mg[Mn(CO)_4PCH_3$ $(C_6H_5)_2]_2$ | Yellow | 57.4 | 5.54 | 2.32 | 10.5 | 5.94 | — | 56.6 | 6.01 | 2.55 | 9.79 | 6.19 | — | — | — |
| $(Pyridine)_4Mg[Mn(CO)_5]_2$ | Light Green | 49.3 | 2.94 | 3.29 | 15.1 | — | 7.67 | 47.6 | 3.11 | 2.91 | 14.9 | — | 7.72 | — | — |
| $(THF)_2Mg[Rh(CO)_2(P(C_6H_5)_3)_2]_2$ | Orange | — | — | 1.58 | 13.4 | — | — | — | — | 1.34 | 14.3 | — | — | — | — |

[a] Molecular weights were determined cryoscopically employing benzene solutions.

SPECIFIC EMBODIMENTS

EXAMPLE 1

Preparation of $[C_4H_8O]_2Mg[Fe(CO)_2C_5H_5]_2$

Method (1)

0.2 gms. $MgBr_2$ dissolved in 15 mls. of tetrahydrofuran was added dropwise to a solution of 0.4 gms. $NaFe(CO)_2C_5H_5$ in 30 ml. of tetrahydrofuran, in a 100 ml. flask equipped with a magnetic stirrer. The $NaFe(CO)_2C_5H_5$ had been prepared by the reductive cleavage Method (2)

A solution containing 5.5 gm of $Hg[Fe(CO)_2C_5H_5]_2$ in 75 ml of tetrahydrofuran was added to a heavy walled reaction tube (equipped with a teflon vacuum stopcock) containing 0.5 gm of 200 mesh magnesium metal. The metal and reaction tube had previously been flamed out under a vacuum of $10^{-6}$ mm. The reaction tube was sealed under vacuum and placed in an oil bath held at 85°C. After 24 hours the tube was broken and the contents filtered. The filtrate was concentrated with reduced pressure. The concentrate was poured into n-pentane which caused the precipitation of a yellow solid. The solid was collected and washed several times with a 25:75 mixture of benzene and n-pentane to remove any unreacted $Hg[Fe(CO)_2C_5H_5]_2$. The final purification procedure was recrystallization from benzene. The yield was 4.2 gm of $[C_4H_8O]_2Mg[Fe(CO)_2C_5H_5]_2$.

Method (3)

1.0 gm of magnesium powder (200 mesh) was placed in a heavy wall reaction tube. The tube and its contents were flamed out at $10^{-6}$ mm. A solution of 6.0 gm of $C_5H_5Fe(CO)_2I$ in 75 ml of tetrahydrofuran was placed in the reaction tube. After a short induction period the reaction became exothermic enough to warm tetrahydrofuran to its reflux point. The initial red solution quickly turned dark yellow and the reaction appeared complete in 15 or 20 minutes. The crude reaction mixture was filtered. $MgI_2$ was collected on the filter and discarded. The filtrate was concentrated with reduced pressure. The concentrate was flooded with n-pentane causing the immediate precipitation of a yellow solid. The crude reaction product was collected and washed with a 50:50 mixture of n-pentane-ether to remove any unreacted $C_5H_5Fe(CO)_2I$. The remaining yellow solid was then recrystallized several times from benzene. The yield was very nearly quantitative Method (4)

In a 250 ml. l-neck, round bottm flask 50 gm of mercury and 0.6 gm of 200 mesh magnesium powder were rapidly stirred to form the amalgam. The amalgam was allowed to cool to room temperature. To the amalgam was added a solution containing 5.0 gm of $[C_5H_5Fe(CO)_2]_2$ in 75 ml of tetrahydrofuran. The resulting solution was deep red. The flask was stoppered and the mixture was stirred vigorously. After 18 hours the solution had become a yellow-green. The reaction mixture was filtered to free it from the amalgam. The filtrate was concentrated with reduced pressure to approximately 25 ml. The concentrated tetrahydrofuran solution was flooded with n-pentane, yielding a yellow solid. The yellow solid was recrystallized from benzene and vacuum dried. The yield was 7.2 gm. of $[C_4H_8O]_2Mg[Fe(CO)_2C_5H_5]_2$.

EXAMPLE 2

Preparation of $(C_5H_5N)_2Mg[Fe(CO)_2C_5H_5]_2$

In a 250 ml, l-neck, round bottom flask an amalgam consisting of 50 gm of mercury and 0.6 gm of powdered magnesium (200 mesh) was prepared. A solution containing 6.7 gm of pyridine in 125 ml of benzene was added to the flask. To the benzene-pyridine solution was added 5.0 gm of $[C_5H_5Fe(CO)_2]_2$. The resultant solution was deep red. After 18 hours the solution had become a reddish-yellow with a considerable amount of a yellow solid suspended in the solution. The reaction mixture was filtered and an orange-yellow solid was collected. The collected solid was taken up in benzene and filtered to free it of magnesium amalgam. The filtrate was concentrated with reduced pressure. The concentrate was flooded with n-pentane, knocking out of solution a bright yellow solid. The solid was recrystallized from benzene and then vacuum dried. The yield was nearly quantitative. The bright yellow solid is air sensitive and is quantitatively oxidized to $[C_5H_5Fe(CO)_2]_2$ and MgO upon exposure to the air. The stoichiometry of the complex was established by nmr measurements and elemental analysis.

EXAMPLE 3

Preparation of $(C_4H_8O)_4Mg[Mo(CO)_3C_5H_5]_2$

This compound was prepared by a method similar to that used in the preparation of $[C_4H_8O]_2Mg[Fe(CO)_2C_5H_5]_2$ described in Method 3 of Example 1. $C_5H_5Mo(CO)_3I$ was prepared by cleaving the molybdenum-molybdenum bond of $[Mo(CO)_3C_5H_5]_2$ with $I_2$ in tetrahydrofuran solution. The magnesium-molybdenum compound is white and is only sparingly soluble in tetrahydrofuran. The stoichiometry of the compound $(C_4H_8O)_4Mg[Mo(CO)_3C_5H_5]_2$ was established by nmr measurements (solutions in d-acetonitrile and elemental analysis. The same product can also be prepared by cleaving $(Mo(CO)_3C_5H_5)_2$ with magnesium amalgam in tetrahydrofuran solution.

EXAMPLE 4

Preparation of $(C_5H_5N)_4Mg[Mo(CO)_3C_5H_5]_2$

This compound was prepared by a method similar to that used in the preparation of the pyridine adduct, $(C_5H_5N)_2Mg[Fe(CO)_2C_5H_5]_2$, described in Example 2 above. The molybdenum cyclopentadienyl tricarbonyl dimer, $[C_5H_5Mo(CO)_3]_2$, was cleaved with magnesium amalgam in benzene solution in the presence of excess pyridine. The solubility of $(C_5H_5N)_4Mg[Mo(CO)_3C_5H_5]_2$ in benzene was found to be somewhat greater than the tetrakis tetrahydrofuran adduct. The pure solid is a light green. The stoichiometry of the compound was determined by nmr measurements upon d-acetonitrile solutions.

EXAMPLE 5

Preparation of $(C_4H_8O)_4Mg[Mo(CO)_2(PCH_3(C_6H_5)_2)C_5H_5]_2$ 0.2 gm of magnesium powder (200 mesh) was flamed out in a heavy walled reaction tube (equipped with a teflon stopcock) under a vacuum of $10^{-5}$ mm. A solution containing 4.0 gm of $C_5H_5Mo(CO)_2(CH_3P(C_6H_5)_2)I$ (prepared by reacting equimolar quantities of $C_5H_5Mo(CO)_3I$ and $CH_3P(C_6H_5)_2$ in benzene solution) in 25 ml of tetrahydrofuran was added to the reaction tube. The stopcock was closed and the tube was placed in an oil bath held at 50°C. to 60°C. After 18 hours the bulk of the magnesium powder had been consumed and an off-white solid had come out of solution. The vessel's contents were filtered leaving $Mg_2$ on the frit. The filtrate was concentrated with reduced pressure. A yellow solid was obtained by flooding the tetrahydrofuran concentrate with n-pentane. This solid was washed with a 50:50 mixture of benzene and n-pentane to remove any unreacted starting material. Nmr and elemental analysis have shown this compound to be the tetrakis tetrahydrofuran adduct. Upon recrystallizing the tetrakis tetrahydrofuran adduct from benzene or allowing a concentrated benzene solution of the compound to stand for several hours, a yellow solid was obtained that has been identified (nmr measurements) as a bis-tetrahydrofuran adduct, $(C_4H_8O)_2Mg[Mo(CO)_2(CH_3P(C_6H_5)_2)C_5H_5]_2$. The tetrakis tetrahydrofuran adduct was also obtained in good yield by substituting a magnesium amalgam for the magnesium powder. The amalgam reaction could be carried out at room temperature.

EXAMPLE 6

Preparation of $(C_4H_8O)_4Mg[CO(CO)_4]_2$

This compound was prepared by cleaving the cobalt-cobalt bond in $Co_2(CO)_8$ with magnesium amalgam in tetrahydrofuran solution. The dark yellow product is extremely air sensitive and is insoluble in all common organic solvents. The air oxidation products are MgO and $Co_2(CO)_8$. The compound's insolubility would not allow a recrystallization, so purification was effected by repeated washings with a 50:50 tetrahydrofuran-n-pentane mixture. The washed solid was extracted with tetrahydrofuran yielding a dark yellow solution (solubility ca. 1 gm/l). A dark yellow solid was isolated by adding n-pentane to the saturated tetrahydrofuran solution. Infrared measurements showed the compound to be free of impurities.

EXAMPLE 7

Preparation of $(C_5H_5N)_4Mg[Co(CO)_4]_2$

This compound was prepared by cleaving $Co_2(CO)_8$ with magnesium amalgam in the presence of excess pyridine in benzene solution. The compound exhibits good solubility in hydrocarbon solvents and was recrystallized from benzene. Elemental analyses were in good agreement with the tetrakis pyridine formulation. The analytically pure compound is light yellow. The compound is air sensitive but less so than $(C_4H_8O)_4Mg[Co(CO)_4]_2$.

EXAMPLE 8

Preparation of $(C_4H_8O)_4Mg[Co(CO)_3PCH_3(C_6H_5)_2]_2$

This compound was prepared by cleaving the cobalt-cobalt bond in $Co_2(CO)_6(CH_3P(C_6H_5)_2)_2$ with magnesium amalgam in tetrahydrofuran solution. $Co_2(CO)_6(CH_3P(C_6H_5)_2)_2$ was prepared by allowing two equivalents of $CH_3P(C_6H_5)_2$ to react with one equivalent of $Co_2(CO)_8$ in refluxing benzene. The substitution reaction was complete in 24 hours. $(C_4H_8O)_4Mg[Co(CO)_3CH_3P(C_6H_5)_2]_2$ was obtained analytically pure by repeated recrystallizations from benzene. The pure compound is yellow. The stoichiometry of the compound was established by elemental analyses and nmr measurements.

EXAMPLE 9

Preparation of $(C_5H_5N)_4Mg[Co(CO)_3PCH_3(C_6H_5)_2]_2$

This was prepared by reducing a benzene solution of $Co_2(CO)_6(PCH_3(C_6H_5)_2)_2$ with magnesium amalgam in the presence of a two-fold excess of pyridine. A light yellow, air sensitive solid was isolated by concentrating the filtered reaction mixture with reduced pressure and flooding the concentrate with n-pentane. The product was purified by recrystallizing from benzene. The yeild was nearly 100%. The molecular formula was obtained by nmr measurements and elemental analyses.

EXAMPLE 10

Preparation of $[(CH_3)_2NCH_2CH_2N(CH_3)_2]_2Mg[Co(CO)_3PCH_3(C_6H_5)_2]_2$

This light yellow compound was obtained in a manner very similar to that used in preparing $(C_5H_5N)_4Mg[Co(CO)_3PCH_3(C_6H_5)_2]_2$ but with tetramethylethylenediamine being substituted for pyridine. The stoichiometry of the compound was established by elemental analyses and nmr measurements.

EXAMPLE 11

Preparation of $(C_4H_8O)_4Mg[Mn(CO)_5]_2$

A 0.1 molar solution of $Mn_2(CO)_{10}$ in tetrahydrofuran was reduced with excess 1% magnesium amalgam. After 18 hours the reaction mixture was filtered and a yellow filtrate was obtained. The filtrate was concentrated with reduced pressure. The concentrate yielded a yellow solid upon addition of n-pentane. The air sensitive yellow solid was found to be only sparingly soluble in benzene. Purification was effected by washing the solid with a 50:50 benzene-n-pentane mixture to remove any unreacted $Mn_2(CO)_{10}$. The washed solid was redissolved in tetrahydrofuran, filtered and reprecipitated with n-pentane. This redissolving-reprecipitation process was repeated several times. The yield was very nearly quantitative. Elemental analysis established the compound as the tetrakis tetrahydrofuran adduct. Note that the elemental analysis (Table I) establishes that the bis-adduct is not formed, as claimed by Hieber et al. Infrared spectral studies also confirm that the tetrakis adduct is the only product formed.

EXAMPLE 12

Preparation of $(C_4H_8O)_4Mg[Mn(CO)_4PCH_3(C_6H_5)_2]_2$

To a slurry of $(C_4H_8O)_4Mg(Mn(CO)_5)_2$ in toluene a two molar equivalent of $CH_3P(C_6H_5)_2$ was added and the mixture was refluxed for two hours. While concentrating the reaction mixture with reduced pressure, a yellow solid came out of solution and was collected by filtration. The stoichiometry of the phosphine derivative was established by elemental analysis and nmr spectroscopy. The addition of phosphine was nearly quantitative. The phosphine derivative has much better solubility in aromatic solvents than the unsubstituted compound.

EXAMPLE 13

Preparation of $(C_5H_5N)_4Mg[Mn(CO)_5]_2$

A 0.1 molar solution of $Mn_2(CO)_{10}$ in benzene containing a small stoichiometric excess of pyridine was reduced with a 1% magnesium amalgam. After 18 hours the reaction mixture was filtered yielding a light green filtrate. Solvent was removed from the filtrate until solid started to come out of solution. N-pentane was added to the concentrated solution, resulting in a nearly quantitative recovery of the desired product. The recrystallized compound is light green. The stoichiometry of the air sensitive compound was established by elemental analysis.

EXAMPLE 14

Hydroformylation of Hexene-1

30 ml of hexene-1, 20 ml of benzene, and 0.3 gm $[C_4H_8O]_4Mg[Co(CO)_3PCH_3(C_6H_5)_2]_2$ were placed in a rocker bomb and pressurized to 1,500 psi with a 1:1 ratio of $H_2:CO$. The bomb was heated to 140°C. and held until the reaction was complete. Analysis indicated that 99% of the hexene-1 was converted to $C_7$ aldehydes and $C_7$ alcohols. 87% of the reacted product was an aldehyde.

EXAMPLE 15

Preparation of $(C_4H_8O)_2Be[Fe(CO)_2C_5H_5]_2$

A small excess of $BeCl_2$ dissolved in tetrahydrofuran is added dropwise to a solution of $NaFe(CO)_2C_5H_5$. The mixture is stirred at room temperature for 24 hours and the bis-tetrahydrofuran adduct of the beryllium-iron substituted carbonyl complex is separated according to the procedure of Method (1) of Example 1.

EXAMPLE 16

Preparation of $(C_4H_8O)_4Mg[Ni(CO)C_5H_5]_2$

The experiment described in Method (4) of Example 1 was repeated, substituting [C$_5$H$_5$Ni(CO)]$_2$ for the iron carbonyl complex described therein. The product isolated was (C$_4$H$_8$O)$_4$Mg[Ni(CO)C$_5$H$_5$]$_2$. This product was also produced by use of Method (3) of Example 1 utilizing C$_5$H$_5$Ni(CO)I in place of the C$_5$H$_5$Fe(CO)$_2$I described therein.

EXAMPLE 17

Trimerization of Butadiene 0.5 gm (C$_4$H$_8$O)$_4$Mg[Ni(CO)C$_5$H$_5$]$_2$ and 5 ml of benzene were placed in a small (ca. 50 ml) pressure reactor under a nitrogen atmosphere. To this black solution was condensed 15 ml of butadiene after passage through a drying train of CaH$_2$ and KOH. This mixture was warmed to 60°C. The resulting pressure was ca 65 psi. The mixture was allowed to stir under these conditions for 2½ hours, after which the pressure had dropped to less than 5 psi.

A gas chromatographic analysis of the reaction mixture showed essentially complete conversion of butadiene into the following cyclic oligomers:

| Oligomer | % (weight) |
| --- | --- |
| vinyl cyclohexene | 7.6 |
| 1,5-cyclooctadiene | 9.9 |
| trans,trans,trans,1,5,9-cyclo-dodecatriene | 78.5 |
| cis,trans,trans,1,5,9-cyclodo-decatriene | 4.0 |

This result is in contrast to the product distribution obtained when (Ni(CO)C$_5$H$_5$)$_2$, the major decomposition product of (C$_4$H$_8$O)$_4$Mg[Ni(CO)C$_5$H$_5$]$_2$ is employed as a catalyst. In the latter case, the primary products are dimers (see table below).

| Oligomer | % (weight) |
| --- | --- |
| vinyl cyclohexene | 69 |
| 1,5-cyclooctadiene | 27 |
| trans,trans,trans,1,5,9-cyclo-dodecatriene | 4 |

EXAMPLE 18

Preparation of (C$_4$H$_8$O)$_2$Mg[Rh(CO)$_2$(P(C$_6$H$_5$)$_3$)$_2$]$_2$ 4.0 gms of ((C$_6$H$_5$)$_3$P)$_2$Rh(CO)Cl was reduced with 70 gms of a 1% magnesium amalgam in 60 ml of tetrahydrofuran under 70 psig carbon monoxide. The initial yellow slurry rapidly became a red homogeneous solution. The crude reaction mixture was filtered. The filtrate was reduced to one-third its initial volume with vacuum and flooded with n-pentane. Upon adding n-pentane, an orange solid precipitated out of solution. The yield of yellow solid was 3.3 gms. The yellow solid is extremely air sensitive.

EXAMPLE 19

Hydroformylation of Propylene (C$_4$H$_8$O)$_2$Mg[Rh(CO)$_2$(P(C$_6$H$_5$)$_3$)$_2$]$_2$ has been found to be a very active hydroformylation catalyst when compared to a conventional rhodium hydroformylation catalyst such as ((C$_6$H$_5$)$_3$P)$_2$Rh(CO)Cl (see Table).

The reaction products are strictly butyraldehydes.

Reaction Conditions:

1000 psig Total pressure
CO/H$_2$ (50/50 mixture)
60 ml benzene as solvent
0.30–0.45 moles propylene
0.5 mmoles catalyst (based on Rh)

| Catalyst | T°C | (%) n-C4H8O[a] | k (min$^{-1}$)[b] | 5$_{1/2}$ (min)[c] |
| --- | --- | --- | --- | --- |
| ((C$_6$H$_5$)$_3$P)$_2$Rh(CO)Cl | 133 | 56 | 0.0744 | 9.32 |
| (C$_4$H$_8$O)$_2$Mg[Rh(CO)$_2$(P(C$_6$H$_5$))$_2$]$_2$ | 95 | 61 | 0.168 | 4.13 |

[a] % n-C$_4$H$_8$ = percent straight chain isomer, determined by G.C. analysis.
[b] k = pseudo 1st order reaction rate constant.
[c] t$_{1/2}$ = ln 2/k.

The table clearly shows that the (C$_4$H$_8$O)$_2$Mg[Rh(CO)$_2$(P(C$_6$H$_5$)$_3$)$_2$]$_2$ complex is more than twice as active as ((C$_6$H$_5$)$_3$P)$_2$Rh(CO)Cl even at a reaction temperature nearly 40°C. lower. Higher yields of the normal C$_4$H$_8$O isomer result most probably because of the lower reaction temperature.

This invention is not intended to be restricted to the above examples, but rather many modifications will be apparent to the skilled artisan, which do not depart from the spirit of the invention.

What is claimed is:

1. A magnesium Group VIII transition metal carbonyl and substituted carbonyl complex having the following formula:

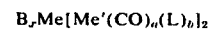

B$_x$Me[Me'(CO)$_a$(L)$_b$]$_2$ wherein B is a Lewis base selected from the group consisting of ether and ketones represented by the general formulae:

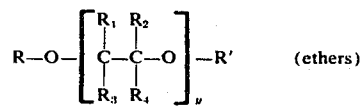

(ethers)

and

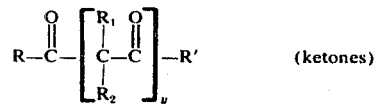

(ketones)

wherein R and R' are C$_1$ to C$_{10}$ hydrocarbon radicals selected from the group consisting of normal, branched, and cyclic alkyl groups, aryl, alkaryl and aralkyl groups; R$_1$, R$_2$, R$_3$ and R$_4$ are selected from the group consisting of hydrogen and C$_1$ to C$_4$ alkyl groups; y is an integer of from 0–3 provided that when y is O R and R' may together form a ring which may or may not include oxygen; x is a positive integer from 1 to 4; Me is magnesium; Me' is a transition metal selected from the group consisting of the metals of Group VIII of the Periodic Table of the Elements; a is an integer ranging from 1 to 4, b is an integer ranging from 0 to 3, and a+b total 4 or less; and L is a uni- or polydentate ligand or hydrocarbon residue which is selected from the group consisting of compounds of the following general formula:

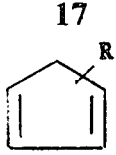

and

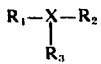

wherein R, R₁, R₂ and R₃ are radicals independently selected from the group consisting of hydrogen, $C_1$ to $C_{20}$ alkyl, $C_3$ to $C_{20}$ cycloalkyl, $C_6$ to $C_{20}$ aryl, $C_7$ to $C_{20}$ aralkyl and alkaryl, and X is selected from the group consisting of N, P, As and Sb.

2. The compound of claim 1 wherein Me' is selected from the group consisting of Fe, [Mo,] Co, Rh and Ni.

3. The compound of claim 2 wherein the Lewis base is tetrahydrofuran.

4. The compound of claim 1 wherein X is phosphorous.

5. The compound of claim 1 wherein R, R₁, R₂ and R₃ are selected from the group consisting of hydrogen, $C_1$ to $C_{10}$ alkyl and $C_6$ to $C_{10}$ aryl, and X is phosphorous.

6. The compound of claim 1, wherein said Group VIII metal is Rh.

7. The compound of claim 1 wherein said Group VIII metal is Ni.

* * * * *